United States Patent [19]

Child et al.

[11] Patent Number: 5,120,895
[45] Date of Patent: Jun. 9, 1992

[54] LOW ACID INVENTORY ALKYLATION

[75] Inventors: Jonathan E. Child; Tomas R. Melli, both of Sewell, N.J.

[73] Assignee: Mobil Oil Corp., Fairfax, Va.

[21] Appl. No.: 664,241

[22] Filed: Mar. 4, 1991

[51] Int. Cl.⁵ .......................... C07C 2/58; C07C 2/56
[52] U.S. Cl. ...................... 585/721; 585/709; 585/720; 585/723; 585/724; 585/726; 585/727; 585/728; 585/730; 585/731; 585/921
[58] Field of Search ............... 585/720, 709, 723, 724, 585/726, 727, 728, 715, 921, 730, 731, 721

[56] References Cited

U.S. PATENT DOCUMENTS

| 2,779,803 | 1/1957 | Bottenberg | 260/639 |
|---|---|---|---|
| 3,249,649 | 3/1966 | Sherk et al. | 585/720 |
| 3,456,033 | 7/1969 | Borst, Jr. | 585/715 |
| 3,696,168 | 10/1972 | Vanderveen | 585/720 |
| 4,024,200 | 5/1977 | Vora | 585/720 |
| 4,276,439 | 6/1981 | Hutson, Jr. et al. | 585/720 |
| 4,795,728 | 1/1989 | Kocal | 502/168 |
| 4,938,935 | 7/1990 | Audeh et al. | 423/240 |
| 4,938,936 | 7/1990 | Yan | 423/240 |

OTHER PUBLICATIONS

Kirk-Othimer, Encyclopedia of Chemical Technology, 3rd ed., New York: John Wiley & Sons, 1980, vol. 12, pp. 154-162 and 171-179.
Shah, B. R., "UOP HF Alkylation Process", Handbook of petroleum refining processes, pp. 1-3 to 1-28 (1986).
Albright, L. F., "Alkylation will be key process in reformulated gasoline era", Oil and Gas Journal, pp. 79-92 (Nov. 12, 1990).
Albright, L. F., "Alkylation of Isobutane with $C_4$ Olefins", 27 Ind. Eng. Chem. Res. pp. 381-397 (1988).

Primary Examiner—Anthony McFarlane
Assistant Examiner—Nhat D. Phan
Attorney, Agent, or Firm—Alexander J. McKillop; Charles J. Speciale; Lori F. Cuomo

[57] ABSTRACT

A process and apparatus are disclosed for acid continuous alkylation of a hydrocarbon-containing feedstream in which the inventory of acid is reduced. The apparatus used combines a reactor, settler and heat exchanger in a single vessel. The acid phase flows out of the reactor only for acid makeup, to account for acid consumption, and regeneration.

13 Claims, 3 Drawing Sheets

LOW ACID INVENTORY ALKYLATION

BACKGROUND OF THE INVENTION

This invention relates to an improved process and apparatus for liquid acid catalyzed continuous alkylation in which the acid inventory is reduced.

Alkylation is a reaction in which an alkyl group is added to an organic molecule Thus, an isoparaffin can be reacted with an olefin to provide an isoparaffin of higher molecular weight. Industrially, the concept depends on the reaction of a C2 to C5 olefin with isobutane in the presence of an acidic catalyst producing a so called alkylate. This alkylate is a valuable blending component in the manufacture of gasolines due not only to its high octane rating but also its sensitivity to octane enhancing additives.

Petroleum refining processes have historically used both sulfuric acid and hydrofluoric acid (HF) as catalysts in commercial alkylation. The sulfuric acid alkylation reaction is particularly sensitive to temperature, with low temperatures being favored to minimize the side reaction of olefin polymerization. Acid strength in these liquid acid catalyzed alkylation processes is preferably maintained at 88 to 94 weight percent by the continuous addition of fresh acid and the continuous withdrawal of spent acid. The hydrofluoric acid process is less temperature sensitive and the acid is easily recovered and purified.

U.S. Pat. No. 4,795,728 to Kocal teaches a hydrofluoric acid catalyzed alkylation process for producing motor fuel. The hydrofluoric acid catalyst complex contains from 0.5 to 5 weight percent of a cationic or anionic surfactant component enabling the process to be operated at an olefin:acid volumetric feed ratio of greater than 1.0 while maintaining acceptable alkylate quality.

For a general discussion of sulfuric acid alkylation, see the series of three articles by L. F. Albright et al., "Alkylation of Isobutane with C4 Olefins", 27 *Ind. Eng. Chem. Res.*, p. 381-397 (1988).

HF alkylation is described in further detail in the *Handbook of Petroleum Refining Processes*, p. 3-28 (1986).

Generally, in modern acid alkylation longer residence times for the hydrocarbon/acid contact are preferred. However, longer residence times result in reduced reactor capacity as well as increased operating costs. For a discussion of residence time see Albright, "Modern Alkylation", *Oil and Gas Journal*, p. 83, (Nov. 12, 1990).

Lewis acid catalyzed alkylation processes are also currently used to produce high octane blending components. Examples of Lewis acids include $BF_3$, $AlCl_3$ and $SbF_5$.

Liquid acid catalyzed continuous alkylation processes generally comprise a reactor, a settler where hydrocarbon droplets are separated from the acid and a heat exchanger where the heat generated by the exothermic reaction is removed. Each vessel requires a large liquid acid catalyst inventory.

Both sulfuric acid and HF alkylation share inherent drawbacks including environmental and safety concerns and acid consumption. While catalyst complexes comprising $BF_3$ overcome some of the safety and environmental drawbacks of sulfuric acid and HF alkylation systems, the volume and quality of $BF_3$ alkylates have not, in the past, proven comparable to that of sulfuric or HF alkylates. Currently HF catalyzed alkylation processes are under particular safety and environmental scrutiny, because of the toxic and corrosive nature of HF.

U.S. Pat. Nos. 4,938,935 and 4,938,936 describe the danger of HF leaks. Though many safety precautions are taken to prevent leaks, massive or catastrophic leaks are feared primarily because the anhydrous acid will fume on escape creating a vapor cloud that can be spread for some distance.

It is therefore an object of the present invention to provide a process and apparatus for reducing the liquid acid catalyst inventory in acid-continuous alkylation processes.

It is a further object to provide a process and apparatus for improving the safety of liquid acid catalyzed continuous alkylation.

It is a further object of the present invention to provide an apparatus for minimizing the risk of a sudden release of toxic material.

SUMMARY OF THE INVENTION

Figure 1:
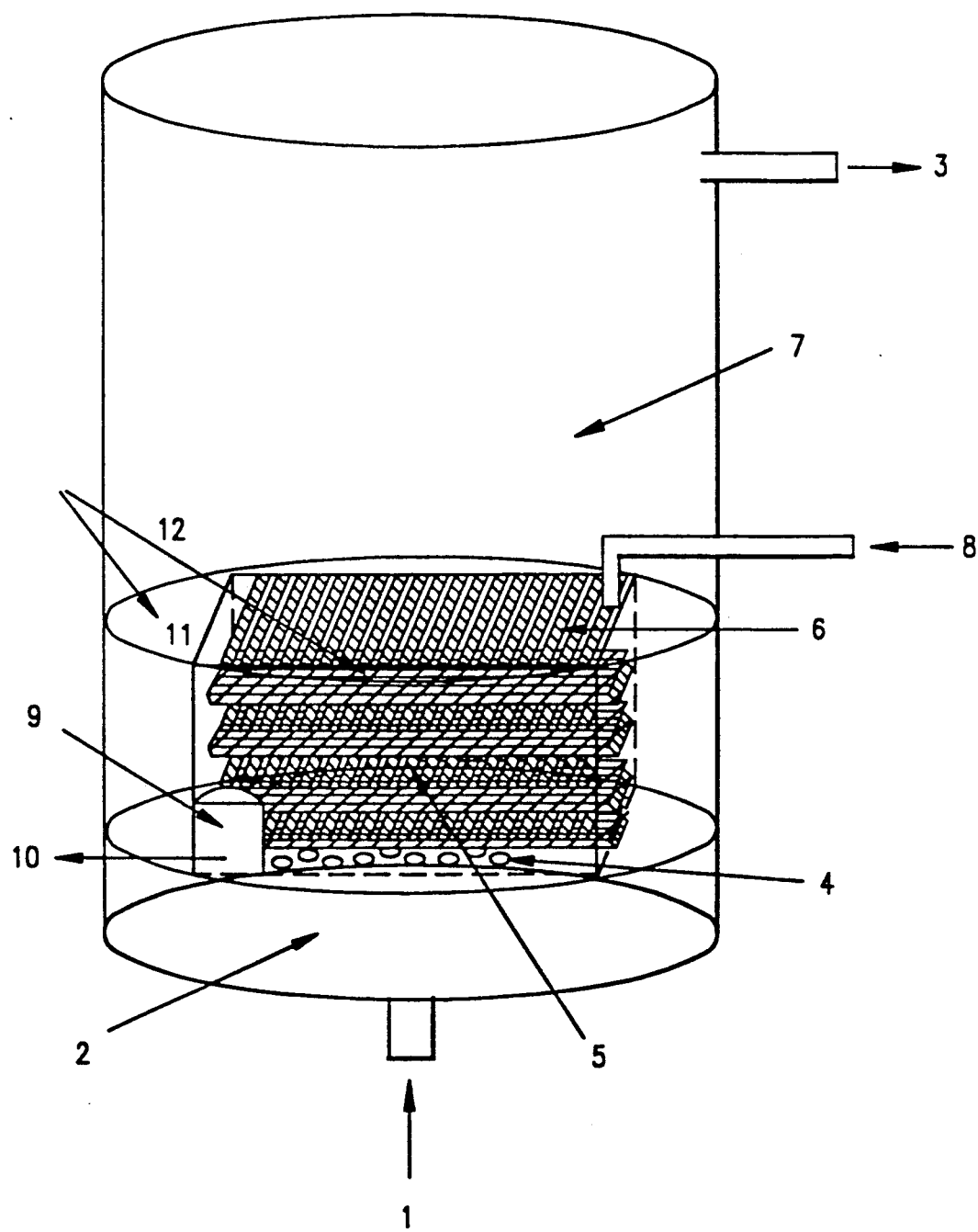
FIG. 1 is a simplified schematic diagram illustrating the shallow pool acid alkylation reactor of the present invention.

The present invention provides an isoparaffin/olefin alkylation process conducted in the presence of a liquid acid catalyst in which the inventory of the alkylation catalyst is reduced by combining the reactor, settler and heat exchanger in a single reaction vessel.

It has unexpectedly been found in accordance with the invention that most of the olefin is converted in the early reaction stages resulting in short contact time alkylation. Thus, while a longer residence time has been desirable in previously known acid alkylation processes the acid alkylation of the present invention surprisingly avoids the need for increased residence time.

The preferred apparatus of the present invention is a low inventory acid alkylation reactor wherein the reaction zone comprises a shallow pool of liquid acid catalyst with cooling and separation in the same vessel. The liquid acid catalyst sits at the bottom of the vessel and the hydrocarbon is bubbled through the acid. The reaction zone is cooled by a bundle of tubes with circulating coolant.

In a further embodiment the apparatus of the present invention resembles a shell and tube heat exchanger. Shell and tube heat exchangers are described in more detail in *Kirk Othmer Encyclopedia of Chemical Technology*, Vol. 12, p. 155-159.

The reaction proceeds on the tube side with each tube filled with a small amount of liquid acid catalyst. The hydrocarbon-containing gas enters through a distribution zone and is bubbled through the bottom of each tube. All the tubes discharge in a settling zone to purge acid carried with the hydrocarbon. After settling, the hydrocarbon alkylation product is withdrawn. A coolant is circulated through the shell to keep the reaction temperature controlled.

The invention therefore includes, in a process aspect, a process for reducing the acid inventory in acid continuous alkylation in which hydrocarbon feed is contacted with liquid acid catalyst, comprising the steps of:

passing said hydrocarbon feed comprising a mixture of isoparaffin and olefin through a distribution zone;

bubbling said hydrocarbon feed into a reaction zone comprising said liquid acid catalyst while simultaneously cooling the reaction zone by heat exchange; and separating the hydrocarbon alkylation product from the liquid acid catalyst in a settling zone, wherein the reaction, settling and heat exchange are carried out in the same vessel.

In a first apparatus aspect, the invention comprises an apparatus for reducing liquid acid catalyst inventory in an alkylation reactor, said apparatus comprising:

(a) a conduit for passing a hydrocarbon feed to a distribution zone;

(b) a reaction zone at the top of said distribution zone having a plurality of cooling tubes and a shallow pool of liquid acid catalyst;

(c) a conduit for passing coolant in and out of said cooling tubes;

(d) multiple distribution nozzles for bubbling the hydrocarbon feed from said distribution zone into said reaction zone;

(e) a disengaging and settling zone at the top of said reaction zone;

(f) a conduit for withdrawing a hydrocarbon alkylation product from said settling zone;

(g) an acid boot collector for collecting spent liquid acid catalyst and an outlet at the bottom of said reaction zone for removal of spent liquid acid catalyst; and (h) a conduit at the top of said reaction zone for adding makeup and regenerated liquid acid catalyst.

In a second apparatus aspect, the invention comprises an apparatus for reducing liquid catalyst inventory in an alkylation reaction, said apparatus comprising:

(a) a reactor shell;

(b) a plurality of individual tubes containing liquid acid catalyst enclosed in said reactor shell;

(c) a conduit for passing coolant in and out of said reactor shell;

(d) a distribution zone in a lower section of said reactor shell;

(e) a means for retaining said liquid acid catalyst in said tubes;

(f) at least one conduit for passing a hydrocarbon feed to said distribution zone;

(g) an inlet at the bottom of each of said tubes for bubbling the hydrocarbon from said distribution zone into said tubes;

(h) a settling zone;

(i) an outlet at the top of said tubes in open communication with said settling zone for discharging the hydrocarbon from said tubes to said settling zone;

(j) at least one conduit for withdrawing a hydrocarbon alkylation product from said settling zone; and (k) a conduit for catalyst regeneration and replenishment.

DETAILED DESCRIPTION OF THE INVENTION

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, 3-methylhexane, 2-methyl butane, 2 methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44–56, the disclosure of which is incorporated by reference as if set forth at length herein.

The molar ratio of isoparaffin to olefin is generally from about 1:1 to about 100:1, preferably from about 1:1 to about 50:1, and more preferably from about 5:1 to about 10:1.

The present alkylation process is suitably conducted at temperatures of from about $-30°$ to about $200°$ C., preferably from about $0°$ to about $100°$ C., and more preferably below about $50°$ C. to avoid undesirable side reactions. Lower reaction temperatures are preferred to maximize alkylate octane. Lower temperatures are generally preferred, for example temperatures as low as $0°$ C. may be effectively employed. Operating temperature typically falls within the range of about $0°$ to about $50°$ C., with the most preferred operating temperatures falling within the range of about $20°$ to about $30°$ C.

Operating pressure is controlled to maintain the reactants in the liquid phase, and is suitably from about 50 to about 1500 psig, preferably from about 75 to about 250 psig. The catalyst weight hourly space velocity as well as the acid dosage varies with the particular acid catalyst system employed.

The particular operating conditions used in the present process will depend on the specific alkylation reaction being effected. Process conditions such as temperature, pressure, space velocity and molar ratio of the reactants will affect the characteristics of the resulting alkylate, and may be adjusted within the disclosed ranges by those skilled in the art with only minimal trial and error.

A simplified schematic of the overall configuration of the shallow pool acid alkylation apparatus is shown in FIG. 1. The shape, size and distribution of the heat exchange area in the alkylation reactor may vary. The alkylation reactor disclosed is a vertical, cylindrical vessel. The hydrocarbon feed is fed through inlet 1 into the hydrocarbon distribution zone 2 and the alkylate product leaves the vessel through the top of the reactor at outlet 3. The hydrocarbon feed flows through hydrocarbon distribution nozzles 4 and is bubbled into reaction zone 5 comprising a shallow pool of liquid acid catalyst. The reaction zone is comprised of a bundle of cooling tubes 6. On the top of the reaction zone is a disengaging and settling zone 7. Fresh and regenerated liquid acid catalyst are added at the top of the reaction zone through port 8. Spent liquid acid catalyst is collected in an acid boot collector 9 and withdrawn from the bottom of the reaction zone through outlet 10. The coolant enters and exits the cooling tubes through ports 11 and 12, respectively.

The shallow pool alkylation reactor can be operated in countercurrent, cocurrent or semicontinuous mode.

The only acid flow permitted out of the reactor is to account for acid consumption and for acid regeneration.

For this invention a shallow pool of liquid acid catalyst is defined as having a length/diameter ratio (L/D) of less than about 1 and preferably about 0.2 when HF is used as the liquid acid catalyst. Conventional L/D ratios are in the range from about 10 to about 20.

In the shallow pool alkylation reactor of the present invention the diameter and the length are chosen to minimize the L/D ratio and satisfy certain hydrodynamic restrictions of L and D. L is the length necessary to complete the reaction in the hydrocarbon bubble rising in the pool of liquid acid catalyst. D is equal to or greater than the minimum diameter necessary to avoid reactor flooding and limit the amount of catalyst carried by the hydrocarbon phase.

The preferred reactor is a vertical, cylindrical vessel. However, other vessel geometries can be used to simplify construction.

The heat transfer area is not limited to the use of a specific tube arrangement. Numerous tube arrangements can be used, such as flat tubes, round tubes and finned tubes. The cooling tubes can be divided into several independent bundles, each with a separate coolant inlet and outlet. Water or other cooling fluid is circulated through the tubes to keep the reaction temperature controlled and to release the heat generated by the alkylation reaction in the liquid acid phase. The arrangement of the tubes contributes to a tortuous hydrocarbon path which increases the droplet residence time and enhances the reaction yield.

The disengaging and settling zone may also have some cooling tubes to account for a higher throughput of hydrocarbon feed which will expand the reaction zone.

Figure 2:
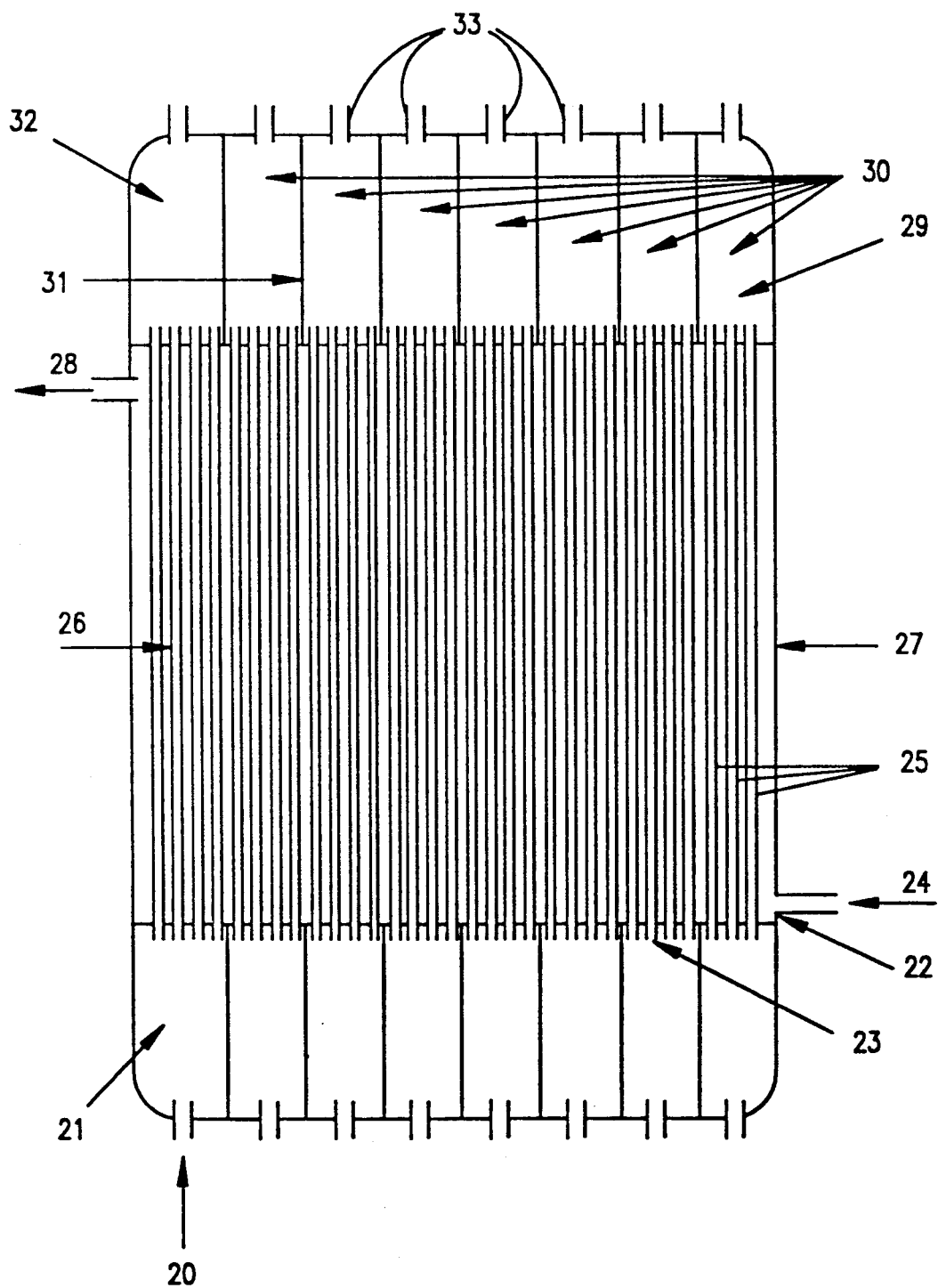
FIG. 2 is a simplified schematic diagram illustrating the multiple tube acid alkylation reactor of the present invention.

In a further embodiment the apparatus resembles a shell and tube heat exchanger. A simplified schematic of the overall configuration of the multiple tube acid alkylation apparatus is shown in FIG. 2. The alkylation reactor is comprised of a shell 27 having enclosed therein a plurality of individual tubes 25 mounted on a plate 22 containing liquid acid catalyst 26. A coolant entering through inlet 24 and exiting through outlet 28 is continuously circulated through the shell side of the reactor. The hydrocarbon feed is introduced into the reactor through inlet 20 into the distribution zone 21. The distribution zone can be divided at least in part by baffles to aid in the flow of hydrocarbon to the individual tubes. The length of the tubes is dependent on the type of liquid acid used as a catalyst. A nozzle 23 at the bottom of each tube disperses the hydrocarbon as droplets in the acid continuous phase. The hydrocarbon is discharged in the settling zone 29 where the hydrocarbon is separated from residual acid carried with the hydrocarbon. The settling zone can be divided at least in part by baffles to aid in the separation. The hydrocarbon alkylation product is discharged through outlets 33.

In an alternative to the use of nozzles at the bottom of each tube to distribute the hydrocarbon in the acid continuous phase, plate 22 can be modified to have apertures. The hydrocarbon is bubbled through the apertures into the individual tubes.

The reactor is divided in several independent sections by complete baffles 31 in the distribution and settling zones. This division allows the reaction to proceed in some sections 30 while the acid is being regenerated in another section 32.

Figure 3:
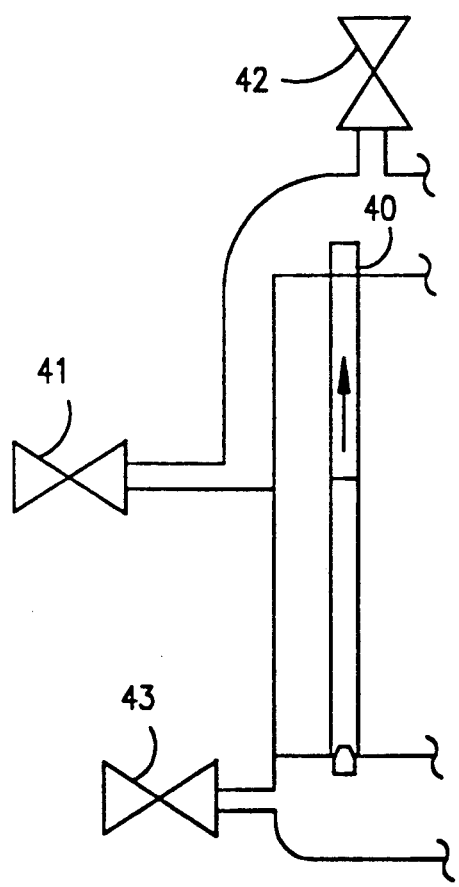
FIG. 3 is a simplified schematic diagram illustrating the regeneration and replenishment cycle in the multiple tube acid alkylation reactor of the present invention.

The section of the multiple tube acid alkylation reactor operating in the regeneration mode is shown in further detail in FIG. 3. When the regeneration is started the olefin portion of the hydrocarbon feed is shut down and the flow rate of the isobutane portion of the hydrocarbon feed is increased to flood the individual tubes. The liquid acid catalyst overflows into the settling zone and the isobutane/acid mixture is collected through downcomer 40 and valve 41. The mixture is then subjected to conventional liquid acid catalyst regeneration. When the outlet stream contains no more acid, valves 41, 42, and 43 are closed and the section is locked under the normal isobutane operating pressure. The regenerated acid is returned to the reactor by pumping the acid through valve 41 with valve 42 partially open. The acid displaces the isobutane, flooding the settling chamber and filling the tubes. When the acid level reaches a maximum value, the excess acid is drained through the downcomer and sent to storage. The isobutane flow is then slowly reestablished and the overflow acid is purged and collected through the downcomer and sent to storage. Finally, olefin feed is reestablished allowing the reaction to proceed in that section.

Water or other cooling fluid is circulated through the shell to keep the reactor temperature controlled and to release the heat generated by the alkylation reaction in the liquid acid phase.

In the multiple tube alkylation reactor of the present invention the acid phase does not flow out of the reactor other than the small amounts for makeup or bleeding for the elimination of acid soluble oils. The acid phase is retained in the tubes of the heat exchanger and the hydrocarbon feed rises as droplets, reacts, and the entire reaction zone is cooled simultaneously. The reaction proceeds in a very thin film around the hydrocarbon droplet.

The fluid velocity of the hydrocarbon feed maintains the liquid acid volume within the tubes via buoyant forces. Additionally, check valves, flapper valves and sintered metal filters may be used to prevent loss of acid into the distribution zone. The amount of liquid acid catalyst in each tube is preferably equivalent in order to maintain a constant pressure drop. If the level of liquid acid catalyst varies significantly from tube to tube, the hydrocarbon feed mixture will favor the tube with the smallest pressure drop.

The liquid alkylation catalyst of the present invention is preferably HF or its reaction products. Other suitable liquid acid catalysts include but are not limited to sulfuric acid and Lewis acids, such as $BF_3$.

The apparatus disclosed herein is especially useful for fast alkylation reactions. While not presented to limit the scope of the invention by a recitation of theory, the following proposed mechanism may prove useful in understanding operation of the invention. Under certain hydrodynamic and mass transfer conditions, the conversion versus time in the alkylation process increases as an exponential function.

Generally, alkylation reactions in the acid phase are second order reactions:

$$r_{alk} = k C_o C_i$$

where C are the concentrations in the acid phase and k is the intrinsic reaction rate constant. Usually the olefin is the limiting reactant and the other compound is in large excess. The above equation can be further simplified assuming that the concentration of the alkylating specie is constant. External mass transfer limits the rate of reaction. Olefin mass balance for a typical example, such as isobutane alkylation in HF, is:

$$-\frac{cX_o}{ct} C_d (1/6) \pi d_d^3 = 1.19 \cdot 10^{-3} X_o (k' D_{o\text{-}HF})^{.5} \pi d_d^2$$

where $d_d$ is the droplet diameter, $k'$ is the pseudo-first order rate of reaction, X is the olefin molar concentration, D is the olefin diffusivity in the acid phase and $C_d$ is the hydrocarbon concentration in the droplet. The time required for reaction is:

$$t = -\frac{C d_d}{C_o' (K C_l' D_{oHF})^{.5} 6} \ln \frac{(1 - x_{of})}{(1 - x_{oi})}$$

when $x_{oi} = 0$, the reaction time is $$x_o = 1 - e^{-at}$$

where $a$ is $$a^{-1} = \frac{C d_d}{C_o' (K C_l' D_{oHF})^{.5} 6}$$

Most of the olefin is converted in the early reaction stages which allows short acid/hydrocarbon contact times.

Table 1 shows the conversion versus time when $T_c$ is the time that it takes to react 99.99% of the olefin present in the feed.

TABLE 1

| Olefin Conversion % | % of $T_c$ |
|---|---|
| 60.2 | 10 |
| 90 | 25 |
| 99 | 50 |
| 99.9 | 75 |

The calculated data from Table 1 shows that most of the reaction can be accomplished in relatively short time intervals.

The acid inventory can be further reduced by decreasing the reaction contact time. The reaction contact time can be minimized by using surfactants or mixing with other acids that improve key properties in the acid, such as solubilities, diffusivities and hydrocarbon droplet size.

TABLE 2

| | PROCESS CONDITIONS | |
|---|---|---|
| | Broad | Preferred |
| Temperature, °C. | −30 to 200 | 20 to 30 |
| Pressure, psig | 50 to 1500 | 75 to 150 |

The particular operating conditions used in the present process will depend on the specific alkylation reaction, and will vary within the disclosed ranges depending upon the available feedstock and the desired alkylate quality. Process conditions such as temperature, pressure, space velocity and molar ratio of the reactants will affect the characteristics of the resulting alkylate, and may be adjusted within the disclosed ranges by those skilled in the art with only minimal trial and error.

EXAMPLE 1

This example shows the production of 5000 Barrels per Day (B/D) alkylate in the shallow pool acid alkylation reactor of the present invention. The dimensions of the reactor compare with the dimensions of commercial settlers, i.e. about 12 ft.×47 ft., for similar alkylate production. The bundle of cooling tubes in the reaction zone occupies about 25% of the internal volume of the reactor. The heat transfer area is about 10,000 ft$^2$ and provided by 24 rows of flat tubes with 254 tubes per row. The average length of the tubes is about 8.6 ft. and the heat transfer area per unit length is about 0.2 ft$^2$/ft.

Fresh and regenerated HF are added to the top of the reaction zone. HF and acid soluble oil (ASO) are collected in the acid boot and withdrawn from the bottom of the reaction zone. The total acid flow rate to the regeneration loop is 50 lts/min. and the acid makeup design value is about 40 lbs HF/hr given a typical ASO production of about 170-190 lbs/hr. The process parameters are set forth in Table 3.

TABLE 3

| Production | 5000 B/D alkylate |
|---|---|
| Liquid acid catalyst | HF |
| Reactor dimensions | 11 ft. ID, 40 ft. long |
| Geometry of reaction vessel | Vertical, cylindrical |
| Reaction zone length | 2 ft. |
| Reactor temperature | 90° F. |
| HF volume in reaction zone | 800 gallons |
| Coolant | Water |
| Water inlet temperature ≦ | 75° F. |
| Water flow rate | 2000 m$^3$/hr |
| Hydrocarbon feed | 50000 b/d |
| Hydrocarbon feed temperature | 70° F. |
| Acid strength | 80-90% |
| Acid to Oil Ratio (A/O) ≈ | 3 |
| Hydrocarbon residence time in reaction zone ≈ | 10.2 sec. |
| Average hydrocarbon rising velocity in reaction zone ≈ | 8 cm/sec. |
| Hydrocarbon residence time in disengaging and settling zone ≈ | 17.5 min. |
| Average hydrocarbon velocity in disengaging and settling zone ≈ | 1.1 cm/sec. |
| Acid residence time within reactor ≈ | 1 hour |

EXAMPLE 2

This example shows the production of 2500 B/D alkylate in the multiple tube acid alkylation reactor of the present invention. In this example, the distribution and settling zones of the reactor are divided into 12 independent sections by complete baffles. Two sections are in the regeneration mode while 10 sections are in the reaction mode. The process parameters are set forth in Table 4.

TABLE 4

| Production | 2500 B/D alkylate |
|---|---|
| Tubes length | 3 ft. |
| Shell ID | 120 in. |
| Tubes OD | ¾ in. |
| Number of tubes | 14400 arranged in 12 isolated sections of 1200 tubes each |
| Hydrocarbon residence time | 10 sec |
| Hydrocarbon inlet temperature | 70° F. |
| Liquid acid catalyst | HF |
| Reactor temperature | 90° F. |
| HF volume in reaction zone | 450 gallons |
| Coolant | Water |
| Water inlet temperature ≦ | 75° F. |
| Water flow rate ≈ | 1000 m$^3$/hr |
| Hydrocarbon feed ≈ | 25000 B/D |
| Isobutane to Olefin Ratio (I/O) ≈ | 15 |
| Starting acid strength ≈ | 96% |

TABLE 4-continued

| Final acid strength = | 85% |
|---|---|

Additionally, in both the multiple tube apparatus and the shallow pool apparatus, the separation of a clear hydrocarbon phase is achieved without a complete settling of the liquid acid catalyst. Further, circulation of the liquid acid catalyst is not necessary. Only a limited amount of liquid acid catalyst required for regeneration and replenishment goes in and out of the reaction vessel.

Another advantage of the multiple tube apparatus is the HF is separated in multiple compartments which adds extra protection in case of puncture or breakage of the tubes. If a tube is broken, the acid released is only that contained in the tube. The acid is then absorbed by the cooling fluid water flowing through the shell.

Changes and modifications in the specifically described embodiments can be carried out without departing from the scope of the invention which is intended to be limited only by the scope of the appended claims.

What is claimed is:

1. A process for reducing the acid inventory in an acid continuous alkylation process in a reactor vessel having a distribution zone, a settling zone, a shell and a plurality of individual tubes filled with liquid acid catalyst, which comprises:
    (a) introducing a hydrocarbon feed to a distribution zone of said reactor vessel;
    (b) passing the hydrocarbon feed into said plurality of tubes filled with liquid acid catalyst to form a hydrocarbon alkylation product while continuously circulating a coolant through the shell;
    (c) passing a hydrocarbon alkylation product from said plurality of tubes filled with liquid acid catalyst to the settling zone of said reactor vessel to purge acid carried with the hydrocarbon alkylation product; and
    (d) withdrawing the hydrocarbon alkylation product.

2. The process of claim 1, wherein the liquid acid catalyst phase does not flow out of the reactor except for acid regeneration and to account for acid consumption.

3. The process of claim 1 wherein the hydrocarbon feed is contacted with the liquid acid catalyst in a countercurrent, cocurrent or semi-continuous mode.

4. The process of claim 1 wherein the liquid acid catalyst is selected from the group consisting of HF, sulfuric acid, Lewis acids and mixtures thereof.

5. The method of claim 1 wherein the liquid acid catalyst comprises HF.

6. The method of claim 4 wherein the liquid acid catalyst further comprises a surfactant.

7. The method of claim 1 wherein the liquid acid catalyst is subjected to catalyst regeneration and replenishment.

8. The process of claim 1 wherein reaction temperature is in the range of from about 0° to about 50° C.

9. The process of claim 1 wherein said liquid acid catalyst is in an amount approximately equivalent in each tube.

10. The process of claim 1 wherein said coolant is water.

11. The process of claim 1 wherein baffles are used in said distribution zone to improve flow of said hydrocarbon feed to said tubes.

12. The process of claim 1 wherein baffles are used in said settling zone to improve said purge of acid.

13. The process of claim 1 wherein said alkylation process proceeds in a first tube while said liquid acid catalyst is being regenerated in a second tube.

* * * * *

UNITED STATES PATENT AND TRADEMARK OFFICE
CERTIFICATE OF CORRECTION

PATENT NO. : 5,120,895

DATED : June 9, 1992

INVENTOR(S) : J. E. Child et al

It is certified that error appears in the above-identified patent and that said Letters Patent is hereby corrected as shown below:

Col. 9, claim 1, line 35          "a" should be --the--

Col. 9, line 37, "the" should be --a--

Signed and Sealed this

Eighteenth Day of January, 1994

Attest:

BRUCE LEHMAN

Attesting Officer        Commissioner of Patents and Trademarks